US009874653B2

United States Patent
Vehra (10) Patent No.: US 9,874,653 B2
(45) Date of Patent: *Jan. 23, 2018

(54) DARK CURRENT CORRECTION IN SCINTILLATOR DETECTORS FOR DOWNHOLE NUCLEAR APPLICATIONS

(71) Applicant: Halliburton Energy Services, Inc., Houston, TX (US)

(72) Inventor: Imran Sharif Vehra, Kingwood, TX (US)

(73) Assignee: HALLIBURTON ENERGY SERVICES, INC., Houston, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 15/679,784

(22) Filed: Aug. 17, 2017

(65) Prior Publication Data
US 2017/0343701 A1  Nov. 30, 2017

Related U.S. Application Data

(63) Continuation of application No. 15/108,612, filed as application No. PCT/US2015/049931 on Sep. 14, 2015, now Pat. No. 9,766,366.

(51) Int. Cl.
*G01V 5/08* (2006.01)
*E21B 47/12* (2012.01)
(Continued)

(52) U.S. Cl.
CPC ............. *G01V 5/08* (2013.01); *E21B 47/12* (2013.01); *E21B 47/124* (2013.01); *E21B 49/00* (2013.01);
(Continued)

(58) Field of Classification Search
CPC ............ G01V 5/08; G01T 1/20; G01N 23/203
See application file for complete search history.

(56) References Cited

U.S. PATENT DOCUMENTS 3,786,267 A * 1/1974 Liu .................... G01V 5/06
250/256
3,937,961 A * 2/1976 Benvenutti ............ G01T 1/204
215/12.1

(Continued)

OTHER PUBLICATIONS

U.S. Appl. No. 15/108,612, "Notice of Allowance", dated May 30, 2017, 8 pages.

(Continued)

*Primary Examiner* — Marcus Taningco
(74) *Attorney, Agent, or Firm* — Kilpatrick Townsend & Stockton LLP (57) ABSTRACT

A radiation logging tool is provided that includes a scintillator detector for use on a wellbore tool string to characterize earth formations. The scintillator detector has a shutter to allow for the collection of data differentiating between incident radiation, such as backscatter signal, and system noise, such as dark current, vibration noise, electronics thermal noise, and electrostatic noise. The radiation logging tool provides for a method of calibrating and measuring incident radiation by the removal of system noise. The shutter is positioned between the photosensor and scintillation member of the scintillator detector, and is able to switch between open and closed states while the scintillation detector is deployed. Measurements of signal noise can be used to calibrate the sampling signal of incident radiation on the scintillator detector.

20 Claims, 5 Drawing Sheets

(51) Int. Cl.
*E21B 49/00* (2006.01)
*G01T 1/202* (2006.01)
*G01N 23/203* (2006.01)

(52) U.S. Cl.
CPC .......... *G01T 1/2026* (2013.01); *G01N 23/203* (2013.01); *G01N 2223/304* (2013.01); *G01N 2223/505* (2013.01)

(56) References Cited

U.S. PATENT DOCUMENTS

| | | | | |
|---|---|---|---|---|
| 5,565,870 | A | * | 10/1996 | Fukuhara .............. G01S 7/2926 342/70 |
| 2005/0263692 | A1 | * | 12/2005 | Samworth .............. G01V 5/125 250/269.1 |
| 2010/0193693 | A1 | * | 8/2010 | Jones ........................ G01T 1/20 250/367 |

OTHER PUBLICATIONS

Arnaboldi et al., "Characterization of a Hamamatsu R7600 Multi-Anode Photomultiplier Tube with Single Photon Signals", Nuclear Science Symposium Conference Record (NSS/MIC), IEEE, Oct. 30, 2010-Nov. 6, 2010, pp. 1124-1129.
Bourdessoule et al., "PMT electronics for high-resolution powder diffraction of CRISTAL and MARS beam-lines", 2013, 4 pages.
Bueno et al., "Characterization of large area photomultipliers and its application to dark matter search with noble liquid detectors", Nov. 27, 2007, 19 pages.
PCT/US2015/049931, "International Search Report and Written Opinion", dated May 25, 2016, 9 pages.
Prout et al., "Readout of the Optical PET (OPET) Detector", Feb. 2005, 12 pages.
Soesbe, "Development and Evaluation of an EMCCD based Gamma Camera for Preclinical SPECT Imaging", Aug. 8, 2007, 239 pages.

* cited by examiner

FIG. 7

DARK CURRENT CORRECTION IN SCINTILLATOR DETECTORS FOR DOWNHOLE NUCLEAR APPLICATIONS

CROSS-REFERENCE TO RELATED APPLICATIONS

This application is a continuation of U.S. patent application Ser. No. 15/108,612 (currently allowed), titled "Dark Current Correction in Scintillator Detectors for Downhole Nuclear Applications" and filed Jun. 28, 2016; which is a U.S. national phase under 35 U.S.C. § 371 of International Patent Application No. PCT/US2015/049931, titled "Dark Current Correction in Scintillator Detectors for Downhole Nuclear Applications" and filed Sep. 14, 2015, the entireties of which are incorporated herein by reference.

TECHNICAL FIELD

This disclosure relates to apparatus and systems for nuclear signal detection and related sensory apparatus for use with a drilling system, or other such well system tool string deployed in hydrocarbon wells and other wells.

BACKGROUND

Photosensitive devices can be used as scintillator detectors for detecting nuclear signals that are used to evaluate formations for wireline and logging while drilling applications. Dark current is inherently generated by a photosensitive device. Dark current can appear as low level noise and can impact low radiation energy measurements of tools such as density tools. Dark current can increase as temperature increases. Some photosensitive devices can be overwhelmed by dark current noise generated at high temperatures. The voltage applied to the photosensitive device can be increased to compensate for the gain of the photosensitive device that is lost due to increased temperature or photosensitive device drift over time. But dark current-generated noise also increases as the voltage applied to the photosensitive device increases.

BRIEF DESCRIPTION OF THE DRAWINGS

Illustrative aspects and examples of the present disclosure are described in detail below with reference to the following drawing figures.

DETAILED DESCRIPTION

A scintillator detector is an instrument used for detecting and measuring ionizing radiation, which in well drilling or hydrocarbon wellbore applications can particularly focus on collecting gamma ($\gamma$) or neutron radiation. A scintillator detector can include a scintillator element, such as the scintillation crystal, that generates photons of light in response to incident radiation. The photosensor of the scintillation detector can receive photons from the scintillator element and convert that light into an electrical signal, and often can amplify it. The scintillator detector can be used with electrical components that can transmit, store, and process the electrical signal. The output of a scintillator detector can be referred to as counts. Scintillator detectors can measure both the intensity and the energy of incident radiation. In wellbore applications, the incident radiation can be backscatter signal radiation. In particular, a radiation logging tool on a tool string can emit a nuclear radiation signal into the surrounding earth strata, and the emitted signal can reflect, refract, or diffract (e.g., scatter) off of the earth strata or formations in the earth strata. The amount redirected back toward the tool string is a backscatter signal. The backscatter signal can be a component of a standard sampling signal. Scintillator detectors can characterize formations in earth strata (e.g., by determining the properties or identifying the contents of regions) based on spectral data, density readings, and the like, derived from the backscatter signal. Scintillator detectors can also be used to sample the naturally occurring radiation. In such systems, active logging sources may not be used; however, a reference check source (or seed source) can be used.

Certain aspects of the present disclosure relate to a scintillator detector with a shutter that is between a photosensor and a scintillation crystal and that can be used to correct for dark current in downhole nuclear applications. Dark current is electric current from photosensitive devices inherently and randomly generating electrons and charge-holes when no photons are in fact entering the devices. The shutter can be operable between an open position and a closed position by a voltage. In the open position, the shutter can allow light produced by the scintillation crystal to pass to the photosensor and be measured with the dark current of the photosensor. In the closed position, the shutter can block light from passing to the photosensor, but the dark current of the photosensor can still be measured. The dark current can be measured by the photosensor for a certain amount of time when the shutter is in the closed position. The measured dark current can be subtracted from light measurements during a normal measurement period, such as when the shutter is in the open position, to remove the dark current component of measurements from the measured light. The measured light with the dark current removed can be further processed. Removing dark current or additional types of noise, such as electronic noise and device vibration noise, can statistically improve the accuracy and sensitivity of measurements by photosensitive devices.

In some examples, the shutter can be a liquid crystal shutter that can be activated, in real time, by the voltage to be in the closed position. The output of the photosensor when the shutter is in the closed position can represent the counts due to dark current only. In other examples, the output can represent the dark current and other types of system noise. The dark current can be sampled for a predetermined period of time as part of a self-calibration cycle. The measured dark current and other types of measured system noise can then be subtracted for normal measurement, when the shutter is in the open position. This can be used for bulk count or spectral measurements.

A drill tool can have other sources of noise that interferes with signals collected by sensors on the tool string. Electronic equipment present on the tool string generates electronic noise, such as thermal noise, flicker noise, interference, crosstalk, and the like. Various aspects of the present disclosure may be used in wireline or slickline sampling operations, permanent or semi-permanent production monitoring, logging while drilling (LWD) applications, or measurement while drilling (MWD) applications. In LWD and MWD applications, the vibration of the tool string can generate a vibration noise, which can include electrostatic effects, the movement of wires and corresponding electromagnetic effects, and signals triggered by the physical motion alone. Contact between the tool string and the walls of a wellbore can also be a source of vibration noise. The dark current, electric noise, and vibration noise can be characterized as system noise.

A process to remove noise resulting from any or all of dark current, electronic noise, and vibration noise from a standard sampling signal can include a calibration process. The calibration process can be performed as a cycle in between standard signal sampling of a scintillator detector such that the calibration process is a real-time calibration process. By closing a shutter in the scintillator detector for a calibration cycle, the photosensor coupled to the scintillator element can measure the system noise affecting the device. In some aspects, the calibration cycle can be performed over a range of time that can be milliseconds in scale, seconds in scale, or aggregates thereof. The system noise can be removed from the sampling signal of incident radiation collected when the shutter is open.

The illustrative examples discussed herein are given to introduce the reader to the general subject matter discussed here and are not intended to limit the scope of the disclosed concepts. The following sections describe various additional aspects and examples with reference to the drawings in which like numerals indicate like elements, and directional descriptions are used to describe the illustrative aspects. The following sections use directional descriptions such as "uphole" and "downhole" in relation to the illustrative aspects as they are depicted in the figures, the uphole direction being toward the surface of the well, the downhole direction being toward the toe of the well. The longitudinal axis of the tool string can be referred to as the "centerline" of the tool string. Further, portions of structural elements described herein can be referred to by their general orientation when deployed, e.g. an uphole end or downhole end. Like the illustrative aspects, the numerals and directional descriptions included in the following sections should not be used to limit the present disclosure.

Figure 1:
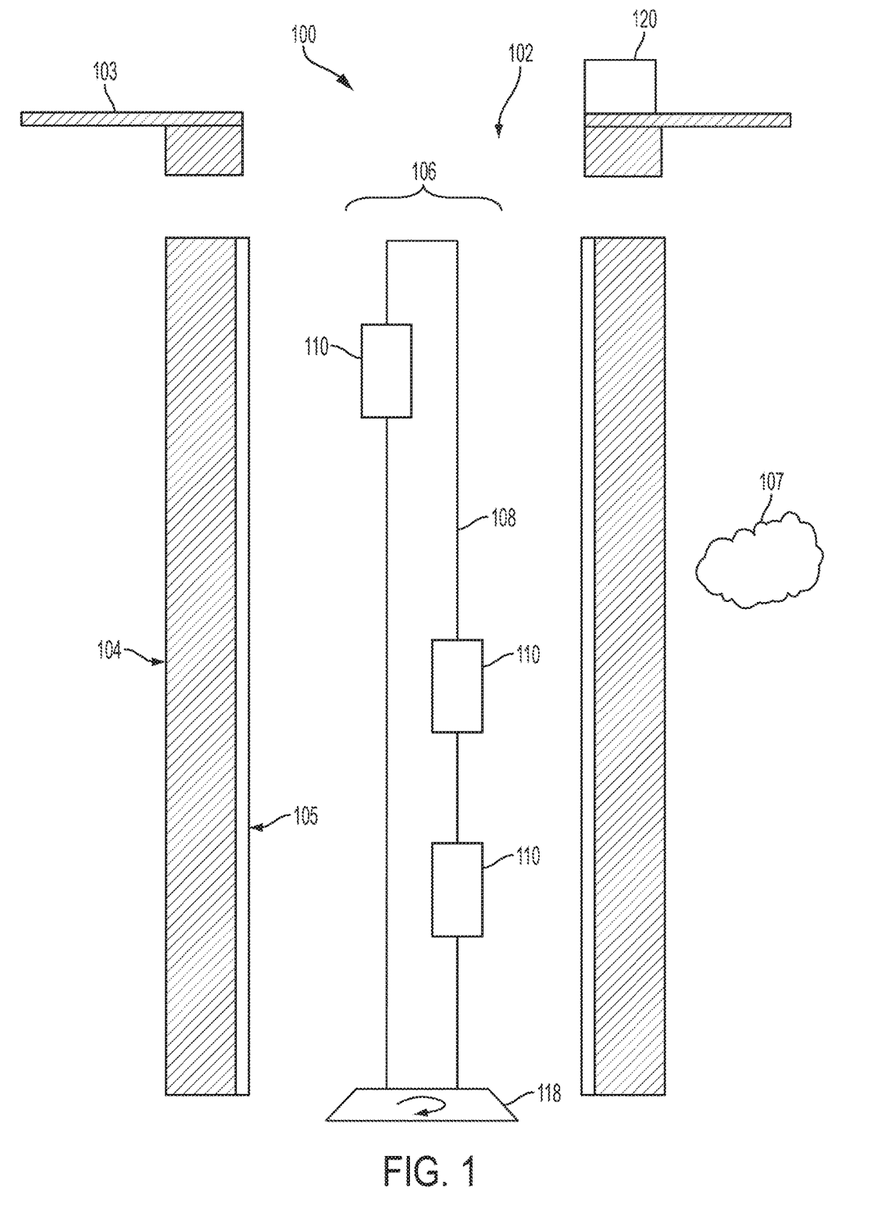
FIG. 1 is a schematic diagram of a well drilling tool string having nuclear signal detectors deployed in a wellbore, according to some aspects of the present disclosure.

FIG. 1 is a schematic diagram of a well drilling system 100 having a tool string 106 deployed in a wellbore 102. The tool string 106 can have sensors. In the well drilling system 100, a wellbore 102 formed in earth strata 104 is drilled by rotating a drill bit 118 coupled to the tool string 106. In some aspects, a well casing 105 can be set and arranged along the sides of earth strata 104 defining the wellbore 102. In other aspects, a well drilling system 100 can be applied in an open hole wellbore.

The tool string 106 can include a mandrel 108 with one or more radiation logging tools 110. The radiation logging tools 110 can be positioned along the mandrel 108, uphole or downhole of other radiation logging tools 110. In some aspects, other sensors, tools, communication apparatus, instrumentation, and other tool string apparatuses (not shown) can be used in well drilling systems anywhere along the mandrel 108 up to the well surface 103 or down to the bottom (or toe) of the wellbore 102. Each radiation logging tool 110 can be mechanically coupled to the mandrel 108 extending radially from the centerline of the mandrel 108, or positioned on components other than the mandrel 108. Each radiation logging tool 110 can include a radiation emitter that emits nuclear signal into the earth strata 104 that scatter off formations 107 within the earth strata. Each radiation logging tool 110 can also include a scintillator detector that has components for measuring the backscatter signals and removing dark current and other noise from the measured signals.

FIG. 1 further shows a drilling tool having a drill bit 118 and radiation logging tools 110 can be operated during drilling (e.g., taking LWD/MWD recordings) and during periods where the drill bit 118 is not actively drilling or rotating within the wellbore 102. The control unit 120 can be located at the surface 103 of the well drilling system 100. The control unit 120 can include a non-transitory computer-readable medium and microprocessors configured to receive data from the radiation logging tools 110 located along the tool string 106. In some aspects, the control unit 120 can further control the operation of the tool string 106 and the drill bit 118, or any other apparatus, tool, or instrumentation coupled to the tool string 106. In some aspects, the control unit 120 can collect or aggregate data received from the radiation logging tools 110 and generate a profile or characterization of the earth strata 104 and formations 107 proximate to the wellbore 102. The control unit 120 can further include a user interface to allow for an operator to monitor and control the function of the tool string 106, and to evaluate any measurements of signals received from the radiation logging tools 110 or other sensory apparatus located downhole.

Figure 2:
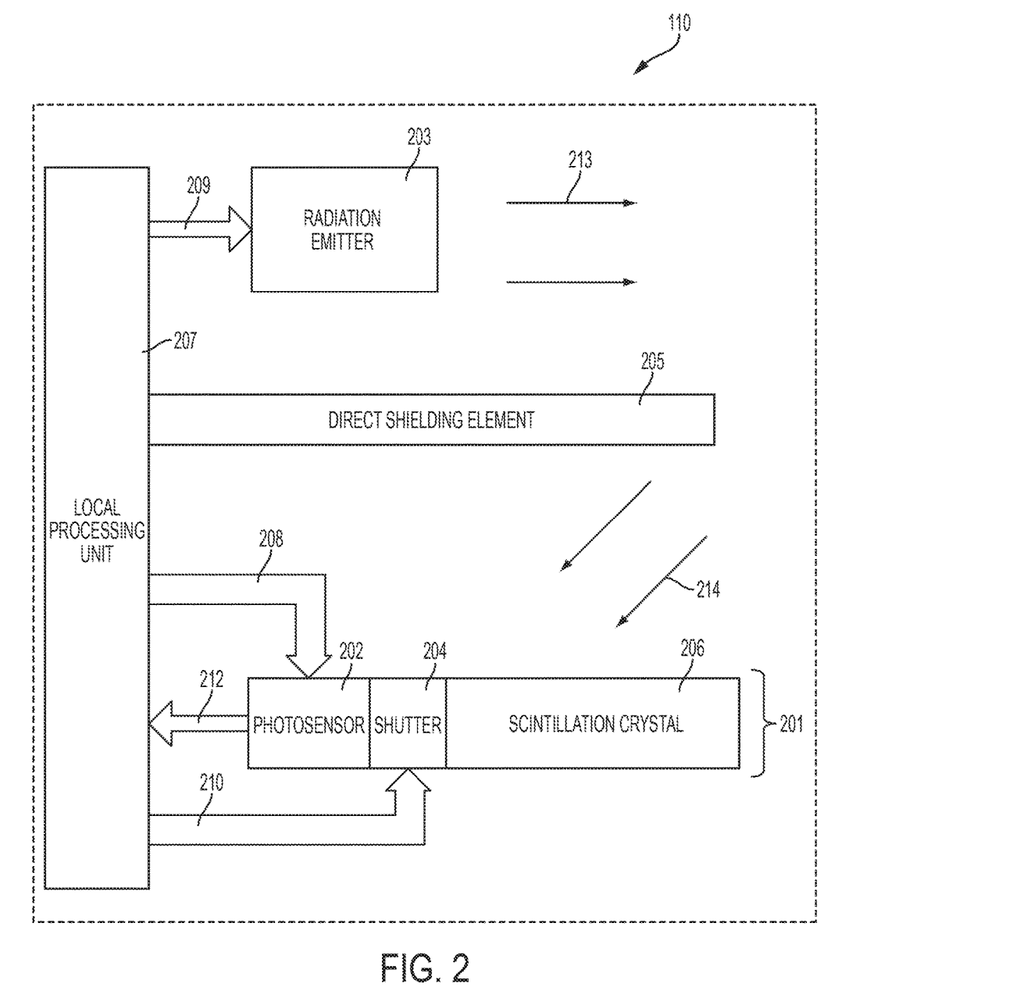
FIG. 2 is a schematic diagram of a radiation logging tool that includes a scintillator detector and a radiation emitter, according to some aspects of the present disclosure.

FIG. 2 is a schematic diagram of the radiation logging tool 110 according to one example. The radiation logging tool 110 includes a scintillator detector 201 and a radiation emitter 203 for emitting nuclear signals 213. The scintillator detector 201 can include a photosensor 202, a shutter element 204, and a scintillation crystal 206. The radiation emitter 203 can be located downhole with the scintillator detector 201 and can emit nuclear signals 213 into the surrounding formations. The signals 213 can reflect, refract, or diffract off of earth strata, as well as formations in the earth strata, as backscatter signals that can be a component of incident signals 214. The incident signals 214 can be received by the scintillation crystal 206 of the scintillator detector 201, leading the scintillation crystal 206 to generate photons. In some aspects, natural gamma radiation of the surrounding earth strata and formations can also be a component of the of incident signals 214. A direct shielding element 205 can be positioned between the radiation emitter 203 and the scintillator detector 201 such that nuclear signals 213 are generally prevented from being directly received by the scintillation crystal 206. Thus, the scintillator detector 201 can collect and measure backscatter signals characterizing the earth strata without noise or interference caused from inadvertent collection of direct nuclear signals 213 from the radiation emitter 203.

In alternative aspects, the radiation logging tool 110 can be constructed without a radiation emitter 203, such that the scintillator detector 201 collects incident signals 214 primarily based on natural gamma radiation.

The shutter element 204 is positioned between and coupled to the scintillation crystal 206 and the photosensor 202. Light can be blocked from entering the photosensor 202 from the scintillation crystal 206 when the shutter element 204 is in a closed configuration. Light can be allowed to pass to the photosensor 202 when the shutter element 204 is in an open configuration. The shutter element 204 can be driven by a shutter control voltage 210 to actuate the shutter between an open configuration and a closed configuration. The scintillator detector 201 can log sample signals based on incident signals 214 while the shutter element 204 is in the open configuration. The scintillator detector 201 can log signals in the photosensor 202 based on system noise (including dark current) while the shutter element 204 is in the closed configuration, which can be during a calibration cycle, for example. An output signal 212 is generated by the photosensor 202, and the scintillator detector 201 transmits the output signal 212 to other electronics, such as the local processing unit 207 or a control unit at the surface of the wellbore, for processing, manipulation, and analysis of the collected output signal 212.

The shutter element 204 can be a liquid crystal shutter, a mechanical shutter, an optical shutter, a piezoelectric, an optical grating, or other such element that can be actuated between an open and a closed configuration. In aspects where the shutter element 204 is a liquid crystal shutter, the liquid crystal shutter can turn opaque or black and block light when the shutter control voltage 210 is applied to the shutter element 204. Applying shutter control voltage 210 to the shutter element 204 can be controlled and executed at any time while the scintillator detector 201 is deployed downhole. In aspects where the shutter element 204 is a mechanical shutter or other optical shutter, the aperture of the shutter element can be opened, closed, or cycled when the shutter control voltage 210 is applied to the shutter element 204. In aspects where the shutter element 204 is a piezoelectric or an optical grating, the optical path of light from the scintillation crystal 206 can be shifted toward or away from the photosensor 202 when the shutter control voltage 210 is applied to the shutter element 204. A particular orientation of the piezoelectric or optical grating element as a shutter element 204 can operate as a closed configuration, even if the optical path does continue to pass through the piezoelectric or optical grating element.

The photosensor 202 can be supplied power at an operational voltage 208 sufficient to power elements of the photosensor 202 to collect signals from the scintillation crystal 206. In some aspects, the power of the operational voltage 208 driving the photosensor 202 can be from a power source coupled to or within a local processing unit 207. The photosensor 202 can be a photomultiplier tube (PMT), and the operational voltage 208 can be sufficient to maintain the relative voltages of dynodes of the electron multiplier within the PMT. In alternative aspects, the photosensor 202 can be a photodiode, an avalanche photodiode, solid state photomultiplier, or other such semiconductor device that can generate an output signal 212 correlated to the incident signal 214. The output signals 212 can be stored, processed, and transmitted by the local processing unit 207 that is electronically coupled to the scintillator detector 201.

The local processing unit 207 can include a processor and a non-transitory computer-readable medium. The local processing unit 207 can receive, store, process, and transmit data and signals such as operational instructions from a control unit located elsewhere in the well drilling system. The local processing unit 207 can further include computer-executable instructions or algorithms to process, convert, transform, or otherwise manipulate data or signals received from the scintillator detector 201. The local processing unit 207 can transmit signals as output signals 212 to the control unit (either directly or indirectly through the bus master), or other data processing module. The output signals 212 can be transmitted as a continuous stream of data, as batches or packages of data, or in any other transmission scheme. In other aspects, the local processing unit 207 of a given radiation logging tool 110 can be electronically coupled to the local processing units 207 of other radiation logging tools 110 on a given tool string and can transmit signals through the other radiation logging tools 110 for processing.

In some aspects, the well drilling system can include a downhole computer (referred to as a "bus master") that is electronically coupled to one or more tools along the tool string and also to a control unit 120 at the surface of the well. The downhole computer (not shown) can include a microprocessor having a non-transitory computer-readable medium that further includes computer-executable instructions or algorithms to store, process, convert, transform, or otherwise manipulate data or signals received from one or more radiation logging tools 110. Data received by the downhole computer from one or more radiation logging tools 110 can be ultimately relayed to the control unit 120.

The local processing unit 207 can correct the output signals 212 derived from standard signal sampling by removing system noise collected during one or more calibration cycles. During a calibration cycle the shutter element 204 is closed, and the output signal 212 is representative of system noise, which includes noise inherent to the photosensor 202 and scintillator detector 201. The local processing unit 207 can calculate and store a correction value based on the output signals 212 collected during a calibration cycle. The correction value can be an average of the output signals 212 collected during a calibration cycle, a median value of the output signals 212 collected during a calibration cycle, a combination of the output signals 212 collected during two or more calibration cycles, a combination thereof, or another statistically calculated value. During standard signal sampling, the shutter element is open, and the output signals 212 are representative of the incident signals 214 triggering photons that transmit through the scintillation crystal 206. During standard signal sampling dark current inherent to the photosensor 202 and other system noise are also part of the output signals 212. The local processing unit 207 can apply the correction value determined from one or more calibration cycles to the output signals 212 collected during standard signal sampling to remove dark current (and other types of system noise) to produce a calibrated set of formation data. The calibrated set of formation data can more accurately represent the incident signals 214.

In some aspects, the calibrated set of formation data can be stored for a period of time on the non-transitory, computer-readable medium located in the local processing unit 207 and subsequently transmitted as a stream of data or as a data package to a control unit electronically coupled to the radiation logging tool 110. In other aspects, once calculated by the local processing unit 207, the calibrated set of formation data can be directly transmitted in real-time to a control unit electronically coupled to the radiation logging tool 110. In further aspects, the calibrated set of formation data can be stored for a period of time on the non-transitory, computer-readable medium located in the downhole computer and subsequently transmitted as a stream of data or as a data package to the control unit 120. The calibration data can also be used as diagnostic value to determine the nominal noise of the radiation logging tool 110 or the operational life of the radiation logging tool 110.

A calibration cycle can be initiated according to external stimulus, such as a threshold temperature of the surrounding environment. In other aspects, the calibration cycle can be initiated manually or directly by an operator through a control interface at the surface of the wellbore. In further aspects, the calibration cycle can be initiated according to an automatic timing sequence, where the timing sequence can be at equal intervals or in a pattern of timing intervals.

The scintillation crystal 206 can be made from any suitable material. Examples of suitable materials include inorganic crystals based on, though not limited to, cesium iodide (CsI), sodium iodide (NaI), sodium iodide doped with thallium (NaI:Tl), zinc sulphide (ZnS), lithium iodide (LiI), or bismuth germinate (BiGeO). The scintillation crystal 206 can further include other elements as a dopant in the crystal structure to modify the electrical characteristics of the scintillation crystal 206. Inorganic scintillation crystals can be selected for use in specific applications. Cesium iodide in crystalline form can be used as a scintillator for the detection of protons and alpha (α) particles. Zinc sulphide can also be used as a detector of alpha (α) particles. Sodium iodide containing an amount of thallium as a dopant can be used as a scintillator for the detection of gamma (γ) waves. Lithium iodide (LiI) can be used as a detector for neutrons. Other examples of suitable materials for the scintillation crystal 206 include transparent inorganic crystals made of anthracene, stilbene, naphthalene, or other aromatic hydrocarbons.

In some aspects, a transparent silicon-based gel pad or grease (not shown) can be located between the photosensor 202 and scintillation crystal 206. The pad or grease pad can provide cushioning and reduce hard impact between the elements of the scintillator detector 201 caused by physical motion, such as the vibration of a drill bit at the end of a drill string.

The radiation emitter 203 can have any one of several sources for emitting nuclear signals 213. In some aspects, the radiation emitter 203 can have an elemental isotope source, which can be used to emit gamma or neutron radiation into the earth strata of a wellbore. In some aspects, the element or isotope can include, but is not limited to, a cesium (Cs) source, a cobalt (Co) source, or an americium source (Am). The elements and isotopes of elements used for the radiation emitter 203 can have an emission with an amount of energy from about tens of kiloelectrovolts to about tens of megaelectrovolts. In other examples, the radiation source can produce gamma radiation having an energy of about sixty kiloelectrovolts (60 keV). Earth strata can also have a component of natural gamma radiation that can be collected as incident signals 214 by the scintillator detector 201. In alternative aspects, the radiation emitter 203 can emit neutron radiation, or the radiation emitter 203 can be a spectral tool.

Figure 3:
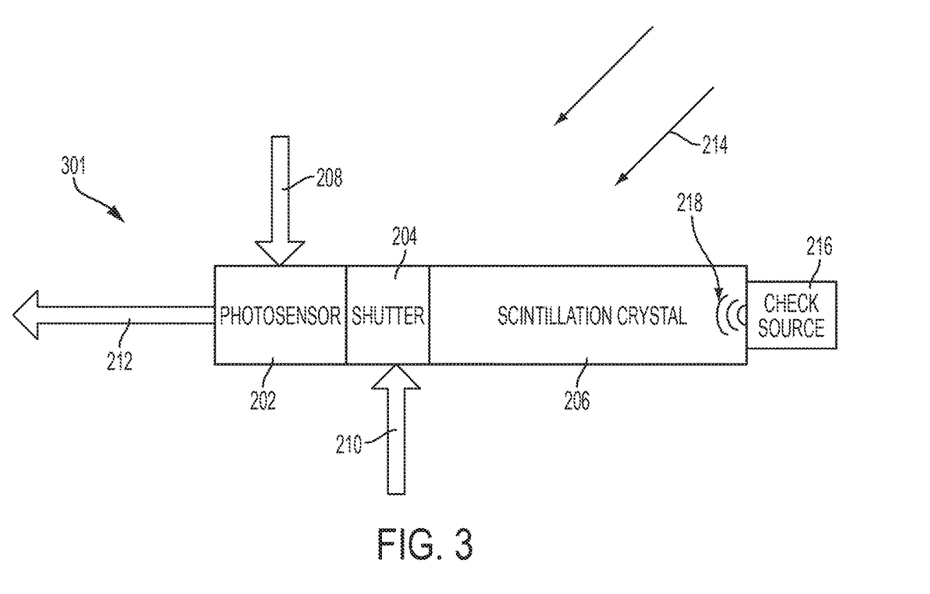
FIG. 3 is a schematic diagram of an example of a scintillator detector that has a check source adjacent to the scintillator detector, according to some aspects of the present disclosure.
Figure 4:
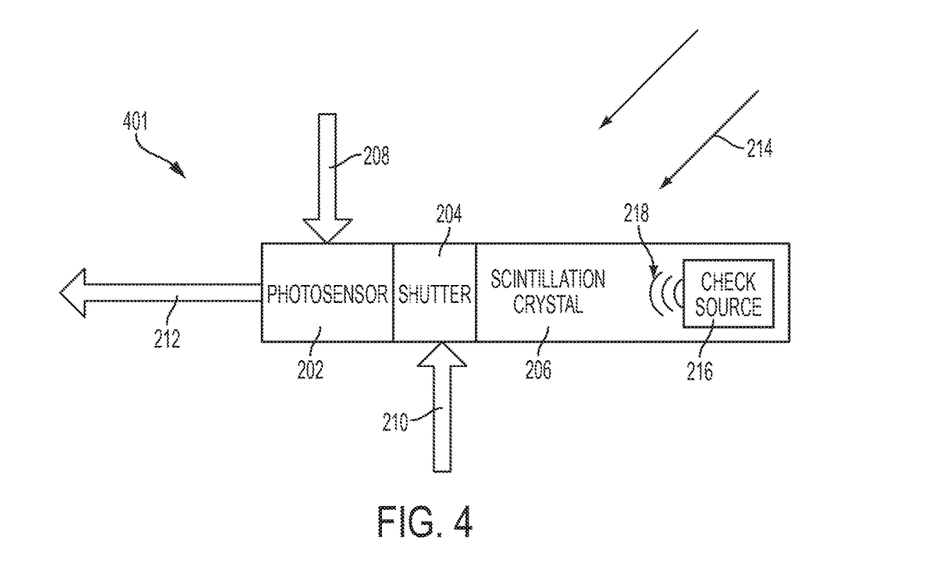
FIG. 4 is a schematic diagram of another example of a scintillator detector that has a check source incorporated with the scintillator detector, according to some aspects of the present disclosure.

Scintillator detectors according to other examples can include a source for a reference signal by which the effectiveness of removing dark current or other types of system noise can be checked. FIG. 3 is a schematic diagram of another example of the scintillator detector 301. The scintillator detector 301 includes the same components as the scintillator detector 201 in FIG. 2, but it also includes a check source 216 adjacent to the scintillation crystal 206. Similarly, FIG. 4 is a schematic diagram of a further example of a scintillator detector 401 that includes the same components as the scintillator detector 201 shown in FIG. 2, but it includes the check source 216 incorporated within the scintillation crystal 206. The check source 216 can provide for additional gain stabilization of the photosensor 202.

For example, the check source 216 can be used in combination with a scintillation crystal 206 to provide a reference signal 218. The check source 216 can emit a small, trace amount of radioactivity proximate to the scintillation crystal 206 as in FIG. 3, or incorporated as part of the scintillation crystal 206 as in FIG. 4. The reference signal 218 provided by the check source can cause the scintillation crystal 206 to generate photons. The check source 216 can emit the reference signal 218 at a lower energy level than the backscatter signal that the respective scintillator detector 301, 401 is configured to detect. In some aspects, however, the check source 216 emits a reference signal 218 that has an energy level in the same range as dark current emissions. Removing dark current noise from the output signals 212 can be confirmed by the removal of an expected reference signal 218 from the check source 216.

The check source 216 can contribute to gain stabilization of the photosensor because the reference signal 218 has a known and stable peak energy, and deviation from that energy level can be used to determine the degree of drift, if any, in a photosensor 202. For applications where the incident signal 214 can have a relatively high energy level, the check source 216 can be selected to emit a relatively low energy level reference signal 218 distinguishable from the expected incident signals 214. If a component of the output signals 212 that is based on the photons triggered by the reference signal 218 indicates drift of the photosensor 202, the operational voltage 208 of the photosensor can be adjusted to alter and stabilize the gain of the photosensor 202.

The check source 216 may emit a reference signal 218 in the same energy level range as expected from the dark current. The reference signal 218 can thereby provide a baseline signal from which the dark current component of the output signals 212 can be calculated. In some aspects, the operational voltage 208 of the photosensor 202 does not need to be increased solely to compensate for a decreased gain. The photosensor 202 can thus be operated at a relatively lower average operational voltage 208 over the course of the photosensor operational life, indirectly extending the operational life of the photosensor 202 by slowing the rate of degradation of the photosensor 202. In some aspects, the check source 216 can include an isotope of an element, such as americium (Am), cobalt (Co), or Cesium (Cs).

Figure 5:
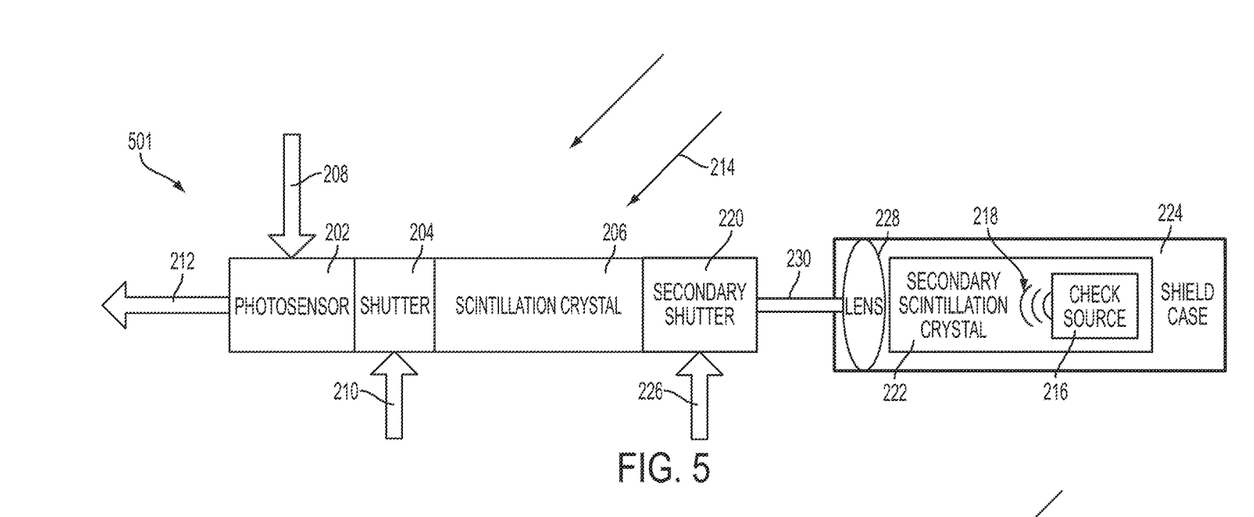
FIG. 5 is a schematic diagram of a further example of a scintillator detector that has an unshielded scintillation crystal arranged in series with a shielded secondary scintillation crystal that has a check source, according to some aspects of the present disclosure.

Scintillator detectors according to various examples can include additional components. FIG. 5 is a schematic diagram of another example of a scintillator detector 501. The scintillator detector 501 is similar to the scintillator detector 401 shown in FIG. 4, except that the scintillation crystal 206 is arranged in series with a shielded secondary scintillation crystal 222 that includes the check source 216. The scintillator detector 501 can also further include a secondary shutter element 220 coupled via an optical fiber 230 to the secondary scintillation crystal 222 and a shield case 224 directly coupled around the secondary scintillation crystal 222. The shield case 224 can surround the secondary scintillation crystal 222, except for the portion of the secondary scintillation crystal 222 coupled to the optical fiber 230 that is further optically coupled to the secondary shutter element

220. Optionally, a lens 228 can be located adjacent to the secondary scintillation crystal 222 within the shield case 224. The optically coupled lens 228 can focus light generated within the secondary scintillation crystal 222 toward the optical fiber 230. When the secondary shutter element 220 is in an open configuration, photons generated in the secondary scintillation crystal 222 can pass through the optical fiber 230 and the secondary shutter element 220 toward the photosensor 202. The scintillation crystal 206 can be an unshielded scintillation crystal in this example. In further alternative aspects, an optional secondary lens (not shown) can be placed between the optical fiber 230 and the secondary shutter element 220 to diverge the light received via the optical fiber 230 (reversing the focusing function of the lens 228) and provide the light to a section of the scintillation crystal 206 wider than the diameter of the optical fiber 230. The optional secondary lens can be located either between the secondary shutter element 220 and the scintillation crystal 206, or between the secondary shutter element 220 and the optical fiber 230.

The reference signal 218 from the check source 216 can be selected to have a minimal number of photons effect the scintillation crystal 206. Minimizing any unintended effect on the scintillation crystal 206 by the reference signal 218 can be accomplished by placing the shield case 224, secondary scintillation crystal 222, and check source 216 at a distance from the other components of the scintillator detector 501 and routing the reference signal 218 through the optical fiber 230 to the secondary shutter element 220. In such aspects, the secondary scintillation crystal 222 can be positioned at a distance one or more foot (1 ft.) away from the check source 216, or far enough such that the counts from the check source have a minimal impact on the scintillation crystal 206.

Light can be blocked from entering the photosensor 202 from the unshielded scintillation crystal 206 when the shutter element 204 is in a closed configuration. Independently, light can be blocked from entering the photosensor 202 from the shielded secondary scintillation crystal 222 (via the unshielded scintillation crystal 206) when the secondary shutter element 220 is in a closed configuration, thereby controlling the times at which a reference signal 218 from the check source 216 passes through unshielded scintillation crystal 206 toward the photosensor 202. The aperture of the shutter element 204 can be opened, closed, or cycled when the shutter control voltage 210 is applied to the shutter element 204. Similarly, the aperture of the secondary shutter element 220 can be opened, closed, or cycled when a secondary shutter control voltage 226 is applied to the secondary shutter element 220. Both the shutter control voltage 210 and the secondary shutter control voltage 226 can be driven by a power source located in the radiation logging tool housing the scintillator detector 501, where the power source can be within a local processing unit 207.

In some aspects, the unshielded scintillation crystal 206 and the shielded secondary scintillation crystal 222 can be constructed of the same scintillation crystal materials. In other aspects, the unshielded scintillation crystal 206 and the shielded secondary scintillation crystal 222 can be constructed of different scintillation crystal materials. In further aspects, a transparent silicon-based gel pad or grease (not shown) can be located between the photosensor unshielded scintillation crystal 206 and the shielded secondary scintillation crystal 222 to provide cushioning and reduce hard impact between the elements of the scintillator detector 501 caused by physical motion or vibration.

In further aspects, the shield case 224 surrounding the shielded secondary scintillation crystal 222 can be made of a high-mass element that blocks the reference signal 218 from passing though the shield case 224 to prevent the reference signal 218 from directly stimulating the generation of photons in the unshielded scintillation crystal 206 when the secondary shutter element 220 is closed. Similarly, in some aspects, the shield case 224 surrounding the shielded secondary scintillation crystal 222 can be made of a high-mass element that blocks incident signal 214 from passing though the shield case 224. The high-mass characteristic of the shield case 224 can prevent the incident signal 214 from producing photons in the secondary scintillation crystal 222 that are not based on the check source 216. In some aspects, the high-mass element used to construct the shield case 224 can be lead (Pb) or another element having sufficient mass to block both the reference signal 218 and an expected incident signal 214. In other aspects, the high-mass element used to construct the shield case 224 can have a thickness to provide a total mass sufficient to block both the reference signal 218 and an expected incident signal 214.

Figure 6:
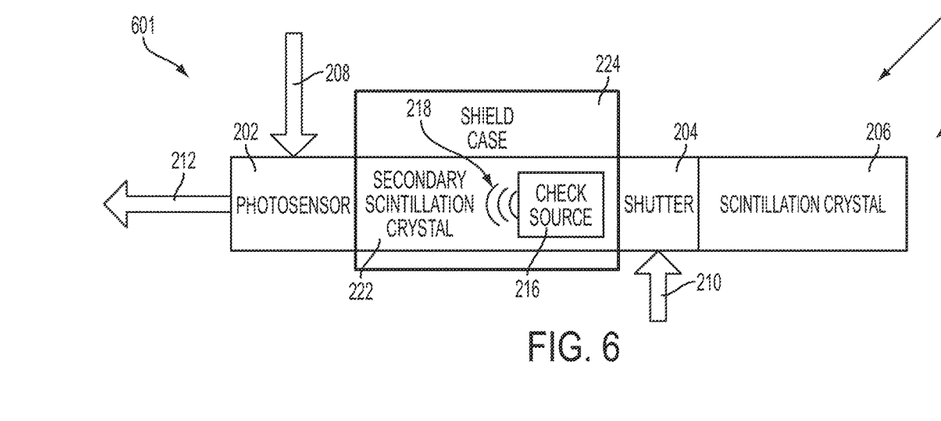
FIG. 6 is a schematic diagram of a further example of a scintillator detector that has a shielded secondary scintillation crystal with a check source arranged in series and with an unshielded scintillation crystal, according to some aspects of the present disclosure.

FIG. 6 is a schematic diagram of another example of a scintillator detector 601. The scintillator detector 601 is similar to the scintillator detector 501 as shown in FIG. 5, except that the secondary scintillation crystal 222 with the check source 216, shielded by shield case 224 is positioned closer to the photosensor 202 than the shutter element 204 and the unshielded scintillation crystal 206 that receives incident signals 214 radiation from the formation and earth strata. In this configuration, when the shutter element 204 is a closed configuration, only the reference signal 218 from the check source 216 and system noise (including dark current from the photosensor 202) is collected. The output signals 212 collected when the shutter element 204 is in the closed configuration can be used for stabilization and can be subtracted from the signal data collected when the shutter element 204 is open. This configuration allows for subtraction of the background signals due to the check source 216.

Figure 7:
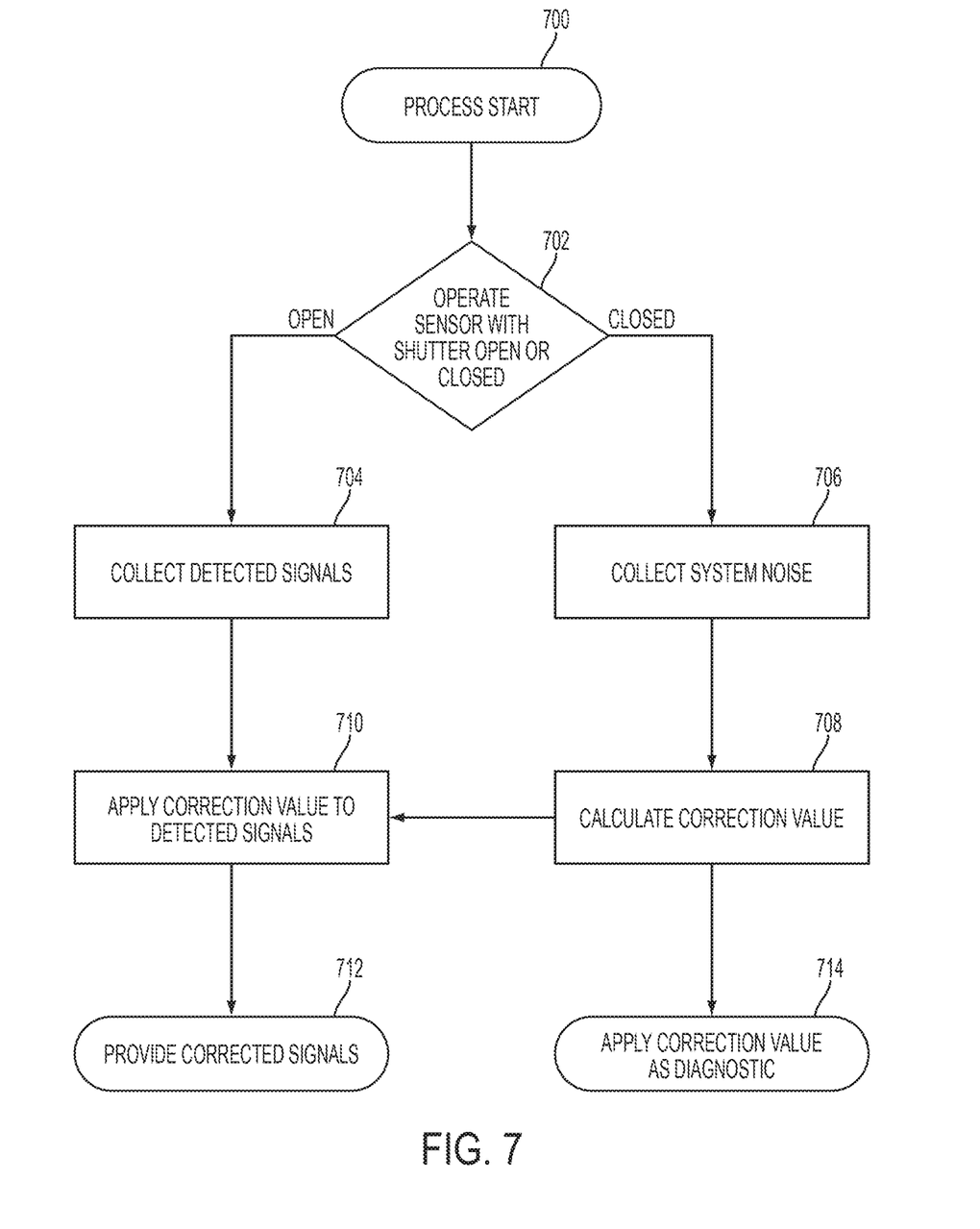
FIG. 7 is a flowchart of a process for collecting sample signal data from a radiation-emitting sensory tool assembly and calibrating the sample signal data to account for device noise, according to some aspects of the present disclosure.

FIG. 7 is a flowchart of a process for collecting sample signals data from a radiation-emitting sensory tool assembly, and calibrating the sample signals data to account for system noise. In some aspects, the sensory tool assembly collects logging data during both standard signals sampling phases and calibration cycle phases, and uses logging data collected during calibration cycle phases to apply a calculated correction to the logging data collected during standard signals sampling. Initially, a tool string having a drilling apparatus is deployed in a wellbore. The tool string can include a radiation logging tool, such as the radiation logging tool 110 of FIG. 2. In block 700, the process starts, where the signal to be detected can be from either or both of radiation logging tool itself and naturally occurring radiation. In block 702, the radiation logging tool is controlled to operate a shutter element of a scintillator detector in an open configuration or a closed configuration.

In block 704, the shutter is operated in the open configuration and detected signal, such as sample signals, are collected from incident signals received from earth strata and formations surrounding the wellbore in which the assembly is deployed. For example, the radiation emitter of the radiation logging tool emits radioactive signals into the surrounding wellbore. The direct signals emitted can reflect, refract, or deflect off of the earth strata and formations of the surrounding wellbore. A portion of the backscatter signal, which can be a component of incident radiation, can be received by the scintillation sensors. The radiation logging tool can emit signals at any time, or at all times, while the drilling apparatus is deployed. The scintillator detector of the sensory tool assembly is receptive to incident signals, which can be an individual signal or a combined signal of backscatter signal, natural gamma radiation, or natural neutron radiation. The scintillation crystal of the scintillator detector emits photons in response to receiving incident signals. A portion of the photons generated in the scintillation crystal enter the photosensor and thereby are measured and recorded as counts at the local processor unit.

The logging data stored in the local processor unit can be processed, which in some aspects can be the application of a correction value to the sample signal data, where the sample signals data is subsequently transmitted to or read by the control unit. In some aspects, operation of the scintillator detector with shutters open can continue for a predetermined period of time. In other aspects, the operation of the scintillator detector with shutters open can be controlled by an operator via a control unit remote from the sensory tool assembly. In various aspects, sample signals data from the local processor unit can be streamed in real-time to the control unit, transmitted in data packages or batches to the control unit, or sent to the control unit in as a combination of both real-time and packaged data transmissions. In other aspects, sample signals data from the local processor unit can be relayed through a downhole computer before being transmitted to the control unit.

In block 706, the scintillator detector, with the shutter element closed, collects signals representative of system noise that includes dark current. For example, while the radiation logging tool may emit radioactive signals into the surrounding wellbore, the photosensor does not receive any photons generated in the coupled scintillation crystal because the shutter element of the scintillator detector is closed. Accordingly, during the calibration cycle, the photosensor is in a configuration where the photosensor detects system noise, while measuring and recording the dark current, vibration noise, and electrostatic noise as counts at the local processor unit.

In block 708, the local processor unit calculates a correction value based on the collected system noise. The correction value can be representative of the vibration noise, electrostatic noise, and any other system noise of the tool string in addition to dark current generated by the photosensor elements of the scintillation sensors. In block 710, the local processing unit can apply the correction value to the sample signals (from block 704) that are detected when the shutter element is open.

The data collected during sample signals collection in block 704 can be further differentiated according to whether the logs were collected while the tool string drilling apparatus was in the process of drilling or not. Similarly, the system noise signals data collected during a calibration cycle in block 706 can be further differentiated according to whether the logs were collected while the tool string drilling apparatus was in the process of drilling or not. The system noise will be different when the tool string drilling apparatus is in the process of drilling or not at least due to the amount of vibration noise present. The local processing unit can calculate and apply a different correction value to sample signals depending on whether or not the drilling apparatus was active at the time of logging.

In block 712, a corrected data set of sample signal processed to remove system noise from the data is provided or transmitted to a processing device, such as a control unit located at the surface of the wellbore. The corrected data set, which can be representative of the characteristics of the earth strata and formations surrounding the wellbore, can be further processed and communicated for analysis of the earth strata and formations surrounding the wellbore.

In block 714, the correction value determined in block 708 can be used to produce a diagnostic value to determine the nominal noise of a given radiation logging tool or the operational life of a given radiation logging tool.

In other examples, collecting detected signals in block 704 also includes a signal from a check source that is used to stabilize the gain of the scintillator detector.

Following completion of either a standard sampling cycle or a calibration cycle, the sensory tool process can return to block 702 periodically, cyclically, in response to a physical stimulus, in response to a programmed sequence, or in response to a user-initiated command.

The subject matter of aspects and examples of this disclosure is described here with specificity to meet statutory requirements, but this description is not necessarily intended to limit the scope of the claims. The claimed subject matter may be embodied in other ways, may include different elements or steps, and may be used in conjunction with other existing or future technologies. Throughout this description for the purposes of explanation, numerous specific details are set forth in order to provide a thorough understanding of examples and aspects of the subject matter disclosed herein. It will be apparent, however, to one skilled in the art that the many examples or aspects may be practiced without some of these specific details. In some instances, structures and devices are shown in diagram or schematic form to avoid obscuring the underlying principles of the described examples or aspects. This description should not be interpreted as implying any particular order or arrangement among or between various steps or elements except when the order of individual steps or arrangement of elements is explicitly described.

The foregoing description of the disclosure, including illustrated aspects and examples has been presented only for the purpose of illustration and description and is not intended to be exhaustive or to limit the disclosure to the precise forms disclosed. Numerous different modifications, adaptations, and arrangements of the components depicted in the drawings or described above, as well as components and steps not shown or described, are possible. Similarly, some features and subcombinations are useful and may be employed without reference to other features and subcombinations. Examples and aspects of the subject matter have been described for illustrative and not restrictive purposes, and alternative examples or aspects will become apparent to those skilled in the art without departing from the scope of this disclosure. Accordingly, the present subject matter is not limited to the examples or aspects described above or depicted in the drawings, and various embodiments, examples, aspects, and modifications can be made without departing from the scope of the claims below.

That which is claimed is:

1. A radiation logging tool, comprising:
　a radiation emitter;
　a scintillator detector comprising:
　　a scintillation member operable to receive nuclear radiation signals from or through an earth formation and to generate photons in response to receiving the nuclear radiation signals;
　　a photosensor for receiving the photons from the scintillation member based on the nuclear radiation signals and for converting the photons to output signals;
　　a shutter, positioned between the scintillation member and the photosensor, that is operable between an open configuration and a closed configuration; and a local processing unit comprising a non-transitory, computer-readable medium with instructions that are executable for causing the local processing unit to:
  in response to the shutter being in the closed configuration, log dark current generated by the photosensor; and
  determine, using the logged dark current from the photosensor, a diagnostic indicator related to a noise of the radiation logging tool.

2. The radiation logging tool according to claim 1, wherein the instructions are executable to cause the local processing unit to determine the diagnostic indicator by calculating a correction value from system noise, and applying a portion of the correction value based on the dark current logged from the photosensor as the diagnostic indicator.

3. The radiation logging tool according to claim 1, wherein the scintillator detector further comprises a check source coupled to the scintillator detector, for emitting a reference signal that is collected by the scintillator detector.

4. The radiation logging tool according to claim 3, wherein the local processing unit includes instructions for calculating a photosensor drift of the scintillator detector and based on the check source reference signal, relative to an expected noise of the radiation logging tool.

5. The radiation logging tool according to claim 3, wherein the local processing unit further includes instructions for evaluating the quality of the output signals based on the check source reference signal, relative to an expected noise of the radiation logging tool.

6. The radiation logging tool according to claim 2, wherein the local processing unit includes instructions for calculating a dark current value relative to an expected noise of the radiation logging tool and evaluating the quality of the output signals based upon the calculated dark current value relative to the expected noise of the radiation logging tool.

7. The radiation logging tool according to claim 1, wherein the diagnostic indicator is further used for determining remaining operational life of the radiation logging tool.

8. A radiation logging tool, comprising:
  a radiation emitter;
  a scintillator detector comprising:
    a scintillation member operable to receive nuclear radiation signals from or through an earth formation and to generate photons in response to receiving the nuclear radiation signals;
    a photosensor for receiving the photons from the scintillation member based on the nuclear radiation signals and for converting the photons to output signals;
    a shutter, positioned between the scintillation member and the photosensor, that is operable between an open configuration and a closed configuration; and
    a local processing unit comprising a non-transitory, computer-readable medium with instructions that are executable for causing the local processing unit to:
      in response to the shutter being in the closed configuration, log dark current generated by the photosensor; and
      determine, using the logged dark current from the photosensor, a diagnostic indicator for determining remaining operational life of the radiation logging tool.

9. The radiation logging tool according to claim 8, wherein determining the diagnostic indicator further comprises calculating a correction value from system noise, and applying a portion of the correction value based on the dark current logged by the photosensor as a calculation of the remaining operational life of the radiation logging tool.

10. The radiation logging tool according to claim 8, wherein the scintillator detector further comprises a check source coupled to the scintillator detector, wherein the check source emits a reference signal that is collected by the scintillator detector.

11. The radiation logging tool according to claim 10, wherein the local processing unit includes instructions for calculating a photosensor drift of the scintillator detector based on a check source reference signal, and applying the photosensor drift to determine the remaining operational life of the radiation logging tool.

12. The radiation logging tool according to claim 10, wherein the local processing unit further includes instructions for determining the remaining operational life of the radiation logging tool based on the check source reference signal, relative to an expected noise of the radiation logging tool.

13. The radiation logging tool according to claim 9, wherein the local processing unit includes instructions for calculating a dark current value relative to an expected noise of the radiation logging tool and determining the remaining operational life of the radiation logging tool based upon the calculated dark current value relative to the expected noise of the radiation logging tool.

14. The radiation logging tool according to claim 8, wherein the diagnostic indicator is further used for evaluating the quality of the output signals of the radiation logging tool.

15. A method of operating a radiation logging tool in a wellbore, comprising:
  emitting a nuclear signal with a radiation emitter into earth strata;
  actuating a shutter element, coupled to and positioned between a photosensor and a scintillator detector, between an open configuration and a closed configuration;
  with the shutter element in the closed configuration, logging dark current with the photosensor;
  calculating a correction value based on the dark current logging; and
  applying the correction value as a diagnostic indicator for output signals emitted by the photosensor with the shutter element in the open configuration.

16. The method according to claim 15, wherein the diagnostic indicator is indicative of the quality of the output signals relative to an expected noise of the radiation logging tool.

17. The method according to claim 15, wherein the diagnostic indicator is indicative of a remaining operational life of the radiation logging tool.

18. The method according to claim 15, further comprising receiving a check source reference signal, and calculating the correction value based on the dark current logging and the check source reference signal.

19. The method according to claim 18, wherein the diagnostic indicator is indicative of the quality of the output signals relative to an expected noise of the radiation logging tool and the check source reference signal.

20. The method according to claim 18, wherein the diagnostic indicator is indicative of a remaining operational life of the radiation logging tool and the check source reference signal.

* * * * *